US009045747B2

(12) United States Patent
Kim et al.

(10) Patent No.: US 9,045,747 B2
(45) Date of Patent: Jun. 2, 2015

(54) APPARATUS AND METHOD FOR FABRICATING MICRO-CAPSULE

(75) Inventors: Choong Kim, Namyangju-si (KR); Ji Yoon Kang, Seoul (KR); Tae Song Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 1836 days.

(21) Appl. No.: 12/154,409

(22) Filed: May 21, 2008

(65) Prior Publication Data
US 2009/0269824 A1   Oct. 29, 2009

(30) Foreign Application Priority Data

Apr. 25, 2008   (KR) .................. 10-2008-0038546

(51) Int. Cl.
*C12N 11/04* (2006.01)
*C12M 1/12* (2006.01)
*B01F 3/08* (2006.01)

(52) U.S. Cl.
CPC ............... *C12N 11/04* (2013.01); *C12M 25/16* (2013.01); *B01F 3/0865* (2013.01)

(58) Field of Classification Search
CPC ...... C12M 23/16; C12M 25/16; C12N 11/04; B01L 3/502776; B01L 3/502784; B01L 2200/0673; B01J 13/04; B01J 13/046; B01J 13/12; B01J 13/20; B01F 3/0865; B01F 2003/0834; B01F 2003/0846
USPC ............... 435/182, 288.5; 422/73, 82; 436/53
See application file for complete search history.

(56) References Cited

U.S. PATENT DOCUMENTS

2006/0051329 A1* 3/2006 Lee et al. .................... 424/93.7
2006/0121122 A1   6/2006 Nakajima et al.

FOREIGN PATENT DOCUMENTS

EP   1 447 127 A1   8/2004
JP   2004-237177     8/2004

OTHER PUBLICATIONS

Decision to Grant a Patent for corresponding Korean application KR 10-2008-0038546 mailed on Feb. 2, 2010 (and English abstract).

* cited by examiner

*Primary Examiner* — William H Beisner
(74) *Attorney, Agent, or Firm* — Merchant & Gould P.C.

(57) ABSTRACT

The present invention relates to an apparatus and a method for fabricating a microcapsule, more particularly to an apparatus and a method for fabricating a microcapsule, which enable to encapsulate uniform cell number in a microcapsule through cell distribution, improve cell viability in the microcapsule through fluid exchange, and ensure uniform microcapsule size. The apparatus for fabricating a microcapsule according to the present invention uses a plurality of microchannels which are spatially connected with one another and are designed such that fluid flows through them in a particular direction, and comprises a cell supply unit which supplies a fluid mixture of cells and a cell dropletizing material; and a droplet forming unit in which a dropletization inducing fluid supplied from one of the plurality of microchannels joins with the fluid mixture of the cells and the cell dropletizing material to form a droplet.

13 Claims, 8 Drawing Sheets

APPARATUS AND METHOD FOR FABRICATING MICRO-CAPSULE

CROSS-REFERENCE TO RELATED APPLICATIONS

This application claims all benefits of Korean Patent Application No. 2008-38546 filed on Apr. 25, 2008 with the Korean Intellectual Property Office, the disclosures of which are incorporated herein by reference.

BACKGROUND OF THE INVENTION

1. Field of the Invention

The present invention relates to an apparatus and a method for fabricating a microcapsule, more particularly to an apparatus and a method for fabricating a microcapsule, which enable to encapsulate uniform cell number in a microcapsule through cell distribution, improve cell viability in the microcapsule through fluid exchange, and ensure uniform microcapsule size.

2. Description of the Prior Art

Microcapsules or microbeads are gaining attention in the field of tissue engineering and cell treatment researches as 3-dimensional cell culturing technique simulating the in vivo tissue environment. To this end, the microcapsules are required to allow the passage of nutrients needed for cell growth, oxygen, drugs and cell exudates, and be semipermeable so as to block the passage of antibodies and immunocytes.

Alginic acid, which satisfies these requirements, is widely used not only as microcapsules but also as scaffolds. Particularly, it is used for transplantation of spleen cells for enabling insulin secretion, targeted drug delivery systems, and the like.

Alginic acid microcapsules are formed by reacting droplet using compressed air or electric field. However, in this case, the resultant capsules have a large size distribution. And, expensive apparatuses are required to form capsules having a diameter of 200 µm or smaller.

To solve this problem, researches on fabricating alginic acid uniform microcapsules smaller than 200 µm using two-phase fluid chips have been reported. However, they are associated with the problem that cell viability inside the microcapsule decreases after encapsulation. And, although it is desirable that a uniform number of cells are encapsulated in a microcapsule in order to attain statistically accurate result, the distribution of clustered cells into individual cells is not considered in these researches.

SUMMARY OF THE INVENTION

The present invention has been made in view of the above problems, and it is an object of the present invention to provide an apparatus and a method for fabricating a microcapsule which enable to encapsulate uniform cell number in a microcapsule through cell distribution, improve cell viability in the microcapsule through fluid exchange, and ensure uniform microcapsule size In an aspect, the present invention provides an apparatus for fabricating a microcapsule using a plurality of microchannels which are spatially connected with one another and are designed such that fluid flows through them in a particular direction, comprising a cell supply unit which supplies a fluid mixture of cells and a cell dropletizing material, and a droplet forming unit in which a dropletization inducing fluid supplied from one of the plurality of microchannels joins with the fluid mixture of the cells and the cell dropletizing material to form a droplet.

The apparatus may further comprise a main channel in which the droplet is solidified by the dropletization inducing fluid to form a microcapsule and the microcapsule is transferred, and a fluid exchange unit in which the dropletization inducing fluid is exchanged with a neutral fluid not reacting with the cells.

The apparatus may further comprise a cell distribution unit which receives the fluid mixture of the cells and the cell dropletizing material from the cell supply unit and distributes the cells individually, the cell distribution unit comprising a plurality of serially connected unit cell distribution channels, the unit cell distribution channel consisting of a circular channel and a stretching channel. The stretching channel is branched from the circular channel. The diameter of the stretching channel is smaller than the diameter of the circular channel, and preferably, the diameter of the stretching channel is 1.5 to 2.5 times the diameter of the cells. A plurality of stretching channels may be branched from one circular channel.

The apparatus may further comprise a cell dropletizing material supply channel which supplies the cell dropletizing material, one end of the cell dropletizing material supply channel being connected to the cell distribution unit and the cell supply unit.

The apparatus may further comprise a neutral fluid supply channel which is branched from one side of the main channel and supplies a neutral fluid to the main channel, and a dropletization inducing fluid discharge channel which is branched from one side of the main channel and discharges the dropletization inducing fluid out of the main channel.

The apparatus may further comprise a capsule collection channel which is equipped at one end of the main channel and collects the microcapsule from the main channel, and a dropletization inducing fluid auxiliary discharge channel which discharges the dropletization inducing fluid remaining without being discharged through the dropletization inducing fluid discharge channel. The dropletization inducing fluid auxiliary discharge channel is connected to one end of the main channel. It is preferable that the diameter of the dropletization inducing fluid auxiliary discharge channel is smaller than the diameter of the capsule collection channel, and the capsule collection channel and the dropletization inducing fluid auxiliary discharge channel are branched from one end of the main channel.

The apparatus may further comprise a cell dropletizing material supply channel which supplies a cell dropletizing material, one end of the cell dropletizing material supply channel being connected to the cell supply unit.

The cell dropletizing material may be alginic acid, the dropletization inducing fluid may be oleic acid, and the neutral fluid may be mineral oil or water.

In another aspect, the present invention provides a method for fabricating a microcapsule using a plurality of microchannels which are spatially connected with one another, comprising the steps of: (a) distributing cells individually in the state where a fluid mixture of the cells and a cell dropletizing material is supplied from one of the plurality of microchannels; (b) joining a dropletization inducing fluid supplied from one of the plurality of microchannels with the fluid mixture of the cells and a cell dropletizing material that has passed through the step (a) to form a droplet; (c) solidifying the droplet, as the droplet and the dropletization inducing fluid flow along one of the plurality of microchannels, to form a microcapsule; (d) exchanging the dropletization inducing fluid in the microchannel of the step (c) with a neutral fluid; and (e) collecting the neutral fluid and the microcapsule through one of the plurality of microchannels.

The microchannel of the step (a) comprises a plurality of serially connected unit cell distribution channels, the unit cell distribution channel consisting of a circular channel and a stretching channel, wherein the circular channel provides a space in which the cells supplied from the stretching channel connected upstream thereof collide with one another and are separated, and the stretching channel is branched from the circular channel and is designed to have a diameter smaller than that of the circular channel, such that the fluid flows faster in the stretching channel and the binding force between the cells therein is weakened. A plurality of stretching channels are branched from one circular channel.

The method may further comprise, between the steps (a) and (b), the step of: (a-1) joining a cell dropletizing material supplied from one of the plurality of microchannels with the fluid mixture of the cells and a cell dropletizing material that has passed through the step (a).

The flux of the cell dropletizing material and the flux of the fluid mixture of the cells and the cell dropletizing material of the step (a) may be controlled to control the number of cells inside the droplet. That is, if the flux of the cell dropletizing material is larger than the flux of the fluid mixture of the cells and the cell dropletizing material of the step (a), the number of cells inside the droplet is decreased. On the contrary, if the flux of the cell dropletizing material is smaller than the flux of the fluid mixture of the cells and the cell dropletizing material of the step (a), the number of cells inside the droplet is increased.

In the step (d) of exchanging the dropletization inducing fluid in the microchannel of the step (c) with a neutral fluid, the dropletization inducing fluid flows leaning to one side pushed by the neutral fluid supplied from one of the plurality of microchannels, and is discharged through one of the plurality of microchannels.

In the step (c), the droplet is solidified as the calcium included in the dropletization inducing fluid reacts with the cell dropletizing material.

The apparatus and method for fabricating a microcapsule according to the present invention provide the advantageous effects of enabling uniform, reproducible encapsulation of cells in a microcapsule through cell distribution, improving cell viability in the microcapsule through fluid exchange, and ensuring uniform microcapsule size.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENTS

In an embodiment of the present invention, an apparatus for fabricating a microcapsule is realized on a microchannel chip having a diameter in the micrometer range. More precisely, the apparatus for fabricating a microcapsule is realized by arrangement of microchannels which are spatially connected with one another. Each microchannel is designed to be aligned along the same direction.

Figure 1:
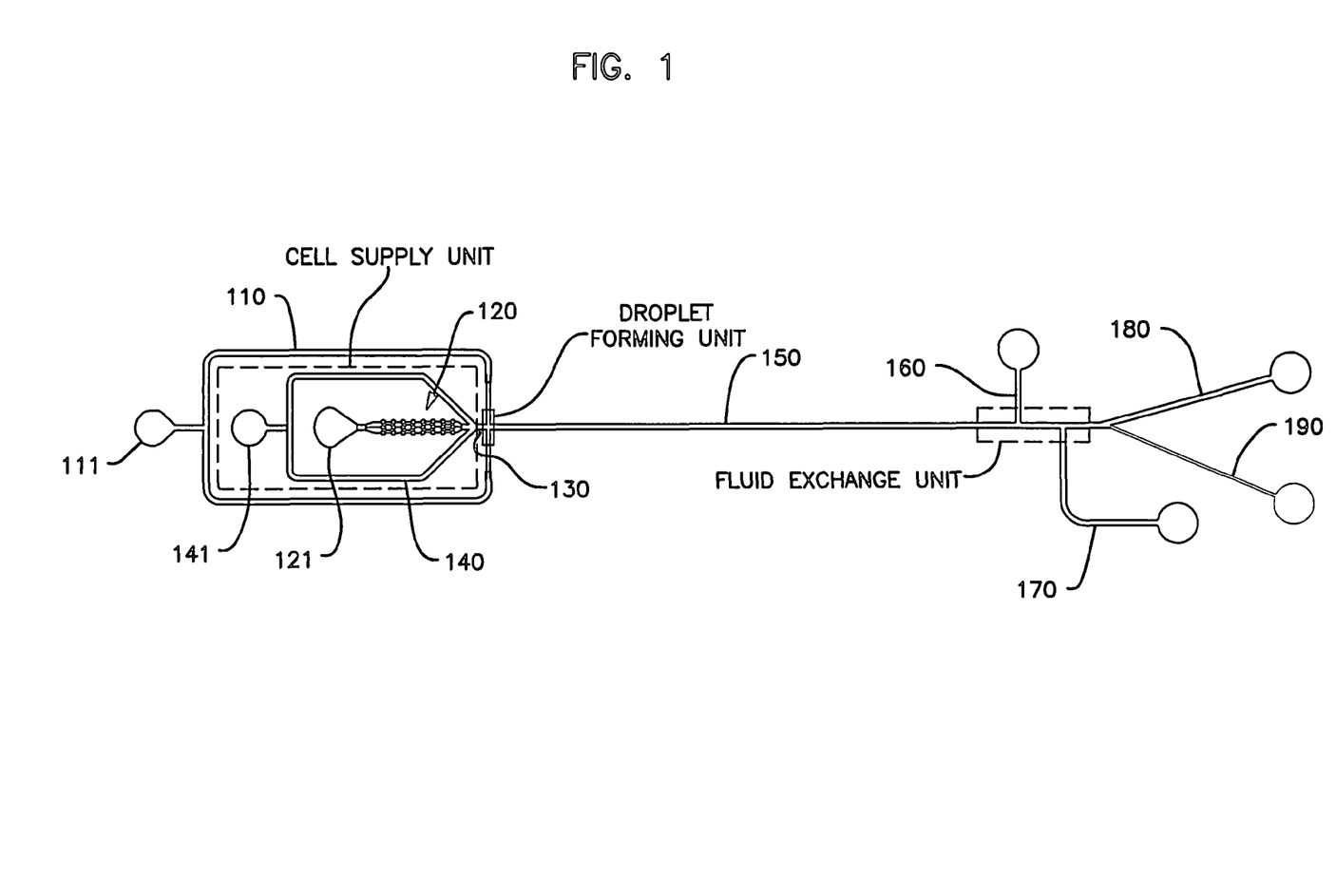
FIG. 1 is a plan view of an apparatus for fabricating a microcapsule according to an embodiment of the present invention.

Referring to FIG. 1, a plurality of microchannels are provided, which are spatially connected with one another. Each microchannel is designed such that fluid flows from the left side to the right side in the microchannel.

The apparatus for fabricating a microcapsule according to an embodiment of the present invention is characterized in preparing microcapsules using such plurality of microchannels. The microcapsules are formed inside the plurality of microchannels through time-series flow and reaction of cell supply, cell distribution, droplet formation, droplet solidification, fluid exchange, capsule collection, and the like.

The apparatus for fabricating a microcapsule according to an embodiment of the present invention in which said cell supply, cell distribution, droplet formation, droplet solidification, fluid exchange, capsule collection, and the like occur will be described in further detail. FIG. 1 is a plan view of an apparatus for fabricating a microcapsule according to an embodiment of the present invention.

As seen in FIG. 1, the apparatus for fabricating a microcapsule according to an embodiment of the present invention comprises a cell supply unit which supplies cells, a droplet forming unit which dropletizes the cells, and a fluid exchange unit which exchanges the fluid that carries the microcapsule. The cell supply unit, the droplet forming unit and the fluid exchange unit are defined with respect to the functions of cell supply, cell distribution, droplet formation, droplet solidification, fluid exchange, capsule collection, and the like and the connection of the plurality of microchannels.

As illustrated in FIG. 1, the apparatus for fabricating a microcapsule according to an embodiment of the present invention comprises a combination of a plurality of microchannels. The respective microchannels are named as dropletization inducing fluid supply channel 110, cell distribution channel 120, cells/cell dropletizing material supply channel 130, cell dropletizing material supply channel 140, main channel 150, neutral fluid supply channel 160, dropletization inducing fluid discharge channel 170, capsule collection channel 180, and dropletization inducing fluid auxiliary discharge channel 190.

To define the cell supply unit, droplet forming unit and fluid exchange unit based on the microchannels illustrated in FIG. 1, the cell supply unit comprises the cells/cell dropletizing material supply channel 130, and the cell dropletizing material supply channel 140 provided upstream of the cells/cell dropletizing material supply channel 130; the droplet forming unit is where the dropletization inducing fluid supply channel 110, the cells/cell dropletizing material supply channel 130, and the main channel 150 join with one another; and the fluid exchange unit comprises the neutral fluid supply channel 160, the dropletization inducing fluid discharge channel 170, and the main channel 150 between the neutral fluid supply channel 160 and the dropletization inducing fluid discharge channel 170.

The connection relationship of the respective microchannels is as follows.

First, the dropletization inducing fluid supply channel 110 is a microchannel through which a dropletization inducing fluid is supplied. One end of the dropletization inducing fluid supply channel 110 is connected to a dropletization inducing fluid inlet 111 and the other end is connected to the cells/cell dropletizing material supply channel 130 and the main channel 150.

The dropletization inducing fluid induces the dropletization of the cells and the cell dropletizing material, as will be described later, as well as transferring the resultant droplet in the main channel 150. For example, oleic acid may be used as the dropletization inducing fluid.

Figure 3:
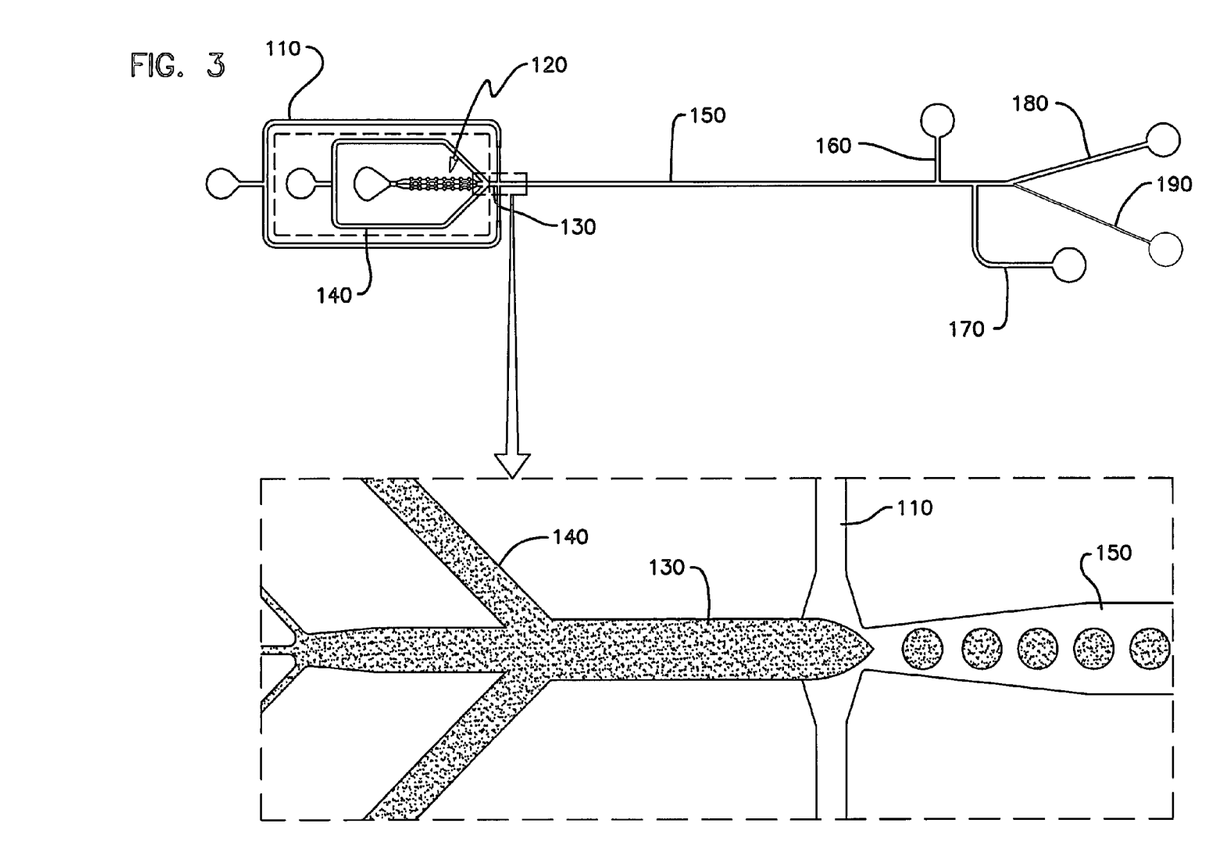
FIG. 3 is an enlarged view of a droplet forming unit according to an embodiment of the present invention.

As described above, the portion where the dropletization inducing fluid supply channel 110, the cells/cell dropletizing material supply channel 130 and the main channel 150 are joined together is defined as the droplet forming unit. In the droplet forming unit, the dropletization inducing fluid supplied from the dropletization inducing fluid supply channel 110 is joined with the fluid mixture of the cells and the cell dropletizing material supplied from cells/cell dropletizing material supply channel 130 to form a droplet. A detailed description thereabout will be given later in the description of the action of the apparatus for fabricating a microcapsule according to an embodiment of the present invention.

Figure 2:
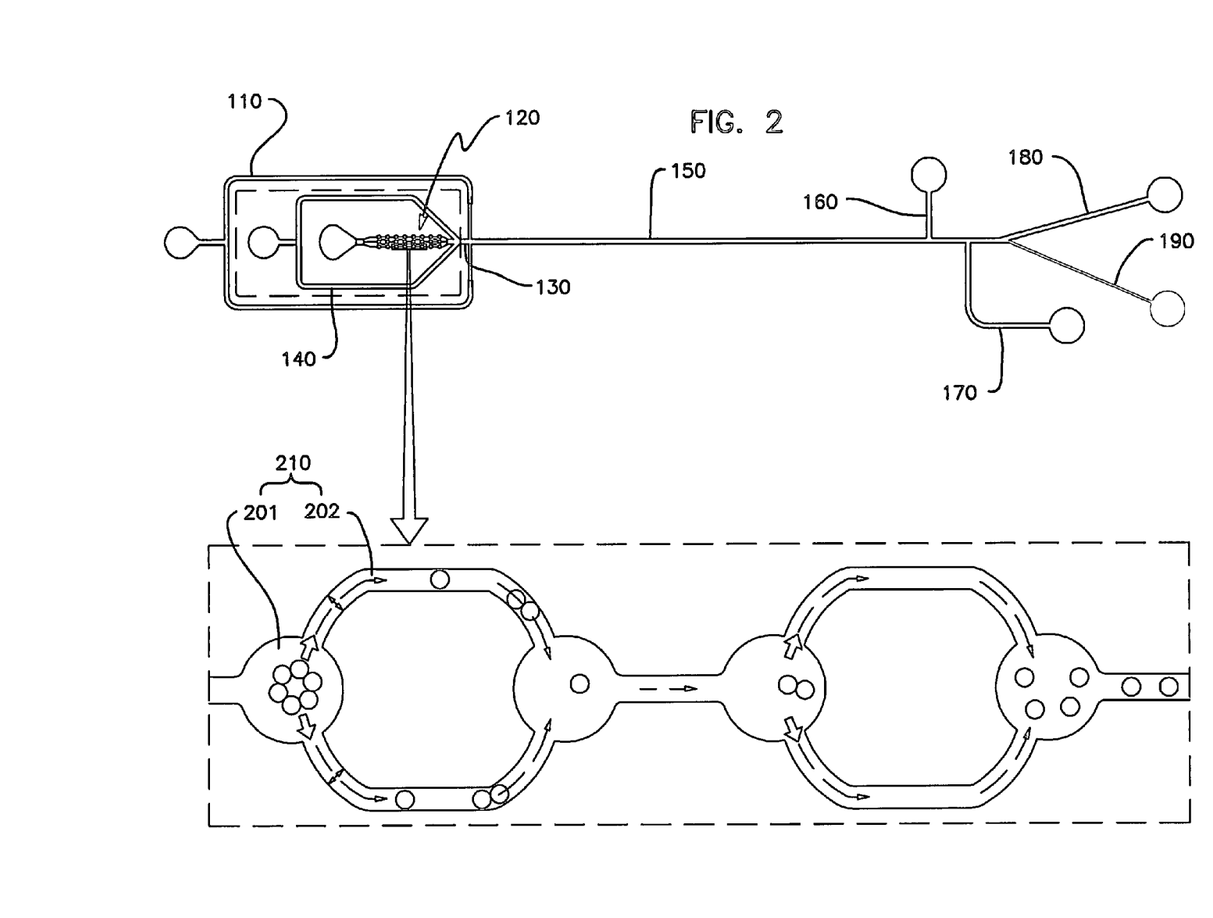
FIG. 2 is an enlarged view of a cell distribution channel according to an embodiment of the present invention.

The cell distribution channel 120 is a microchannel one end of which is connected to the cells/cell dropletizing material inlet 121 and the other end of which is connected to the cells/cell dropletizing material supply channel 130. It comprises a plurality of serially connected unit cell distribution channels 210, each unit cell distribution channel 210 comprising a circular channel 201 and a stretching channel 202. As the fluid mixture of the cells and the cell dropletizing material is supplied from the cells/cell dropletizing material inlet 121, the cells tend to form a cluster with time as they are aggregated together. The cell distribution channel 120 serves to distribute the clustered cells individually.

The cell distribution channel 120 comprises a plurality of unit cell distribution channels 210 which look like repeating chains. A plurality of such cell distribution channels 120 may be aligned in parallel. In this case, one end of each of the cell distribution channels 120 is connected to the cells/cell dropletizing material supply channel 130.

A detailed description about the functions of the circular channel 201 and the stretching channel 202 comprising the cell distribution channel 120 will be given later in the description of the action of the apparatus for fabricating a microcapsule according to an embodiment of the present invention.

The cells/cell dropletizing material supply channel 130 is a microchannel through which the fluid mixture of the cells and the cell dropletizing material is supplied. One end of the cells/cell dropletizing material supply channel 130 is connected to the cell distribution channel 120 and the other end is connected to the dropletization inducing fluid supply channel 110 and the main channel 150. The cell dropletizing material is a material that surrounds the cells and forms a droplet during the dropletization process. For example, it may be alginic acid.

The cell dropletizing material supply channel 140 is a microchannel through which the cell dropletizing material is supplied. One end of the cell dropletizing material supply channel 140 is connected to the cell dropletizing material inlet 141 and the other end is connected to the cells/cell dropletizing material supply channel 130. The cell dropletizing material supply channel 140 is used to selectively vary the concentration of the cells of the fluid mixture of the cells and the cell dropletizing material flowing in the cells/cell dropletizing material supply channel 130. The flux of the cell dropletizing material flowing in the cell dropletizing material supply channel 140 and the flux of the fluid mixture of the cells and the cell dropletizing material flowing in the cells/cell dropletizing material supply channel 130 may be controlled to control the number of cells inside the microcapsule.

The main channel 150 is connected to the dropletization inducing fluid supply channel 110 and the cells/cell dropletizing material supply channel 130. In the main channel 150, the dropletization inducing fluid supplied from the dropletization inducing fluid supply channel 110 flows along with a droplet, which is formed at the droplet forming unit A or the portion where the dropletization inducing fluid supply channel 110 joins with the cells/cell dropletizing material supply channel 130. That is, the dropletization inducing fluid flows together with the droplet inside the main channel 150. The droplet becomes solidified as it flows along the length direction of the main channel 150 and is turned into a microcapsule. A detailed description about will also be given later.

The neutral fluid supply channel 160 is a microchannel through which the neutral fluid is supplied. It is connected to the main channel 150 and serves to replace the dropletization inducing fluid flowing in the main channel 150 with the neutral fluid. Preferably, the neutral fluid is a substance not reacting with the cells. For example, mineral oil mainly consisting of alkane and paraffin or water may be used.

Figure 4:
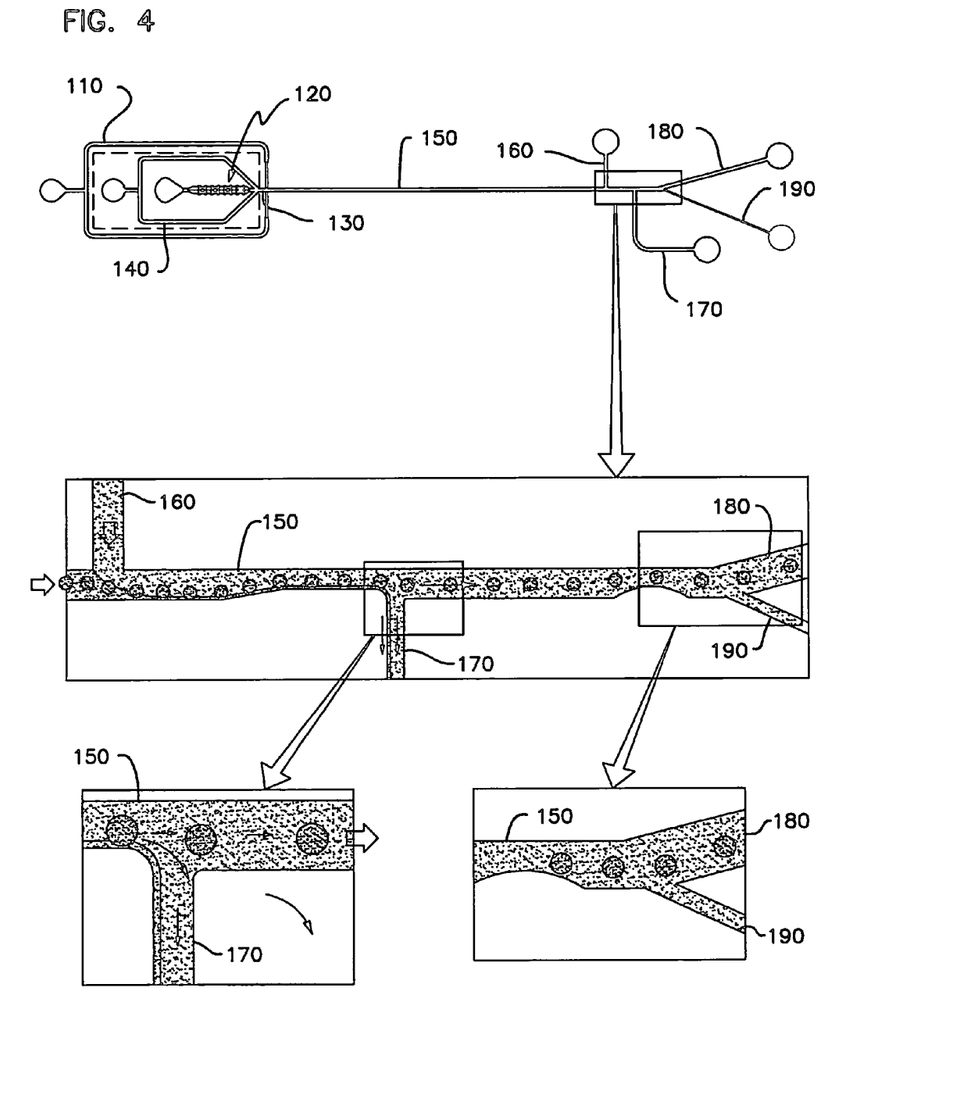
FIG. 4 is an enlarged view of a fluid exchange unit according to an embodiment of the present invention.

The dropletization inducing fluid discharge channel 170 is a microchannel through which the dropletization inducing fluid flowing in the main channel 150 is discharged. The dropletization inducing fluid discharge channel 170 is branched from one side of the main channel 150 and is provided downstream of the neutral fluid supply channel 160 along the length direction of the main channel 150.

The discharge of the dropletization inducing fluid from the main channel 150 to the dropletization inducing fluid discharge channel 170 occurs as follows. As the neutral fluid is supplied from the neutral fluid supply channel 160 to the main channel 150, the flow of the dropletization inducing fluid is pushed from the center of the main channel 150 to one side. The pushed dropletization inducing fluid is discharged through the dropletization inducing fluid discharge channel 170.

The capsule collection channel 180 is a microchannel which is connected to one end of the main channel 150. In the state where the dropletization inducing fluid in the main channel 150 is replaced by the neutral fluid supplied from the neutral fluid supply channel 160, the capsule collection channel 180 receives the neutral fluid and the microcapsule from the main channel 150 and collects the microcapsule. As described in the above, the droplet becomes solidified in the main channel 150 as it flows along the length direction of the main channel 150 and is turned into a microcapsule. The capsule collected by the capsule collection channel 180 is the microcapsule formed as the droplet flowing in the main channel 150 is solidified.

The dropletization inducing fluid auxiliary discharge channel 190 is a microchannel which is connected to one end of the main channel 150. It discharges a small amount of the dropletization inducing fluid which remains without being discharged through the dropletization inducing fluid discharge channel 170. The dropletization inducing fluid auxiliary discharge channel 190 and the capsule collection channel 180 may be branched from one end of the main channel 150. Preferably, the dropletization inducing fluid auxiliary discharge channel 190 is designed to have a smaller diameter than that of the capsule collection channel 180.

In the foregoing, the connection relationship of the respective microchannels of the apparatus for fabricating a microcapsule according to an embodiment of the present invention was described. Hereinafter, the action of the apparatus for fabricating a microcapsule according to an embodiment of the present invention comprising the aforesaid plurality of microchannels will be described.

The action of the apparatus for fabricating a microcapsule according to an embodiment of the present invention comprises the processes of 1) cell distribution, 2) droplet formation, 3) droplet solidification, 4) fluid exchange and 5) capsule collection, in order of time.

Cell Distribution

First, the process of cell distribution will be described.

The fluid mixture of the cells and the cell dropletizing material is supplied from the cells/cell dropletizing material inlet 121 to the cell distribution channel 120. The cells included in the cell dropletizing material tend to form a cluster as they are aggregated with one another as time passes. The cells supplied from the cell distribution channel 120 also form a cluster as they are supplied.

When the a microcapsule is formed through droplet formation and droplet solidification, which will be described later, in the state where the cells are clustered, the number of cells in the microcapsule becomes non-uniform. Accordingly, there is a need to distribute the clustered cells in order to encapsulate a predetermined number of cells.

The cell distribution channel 120 individually distributes the clustered cells. As described earlier, the cell distribution channel 120 comprises a plurality of serially connected unit cell distribution channels 210. Each of the unit cell distribution channels 210 consists of a circular channel 201 and a stretching channel 202.

The clustered cells are distributed individually as the pass through the circular channel 201 and the stretching channel 202 of the unit cell distribution channel 210. Specifically, the circular channel 201 provides a space in which the cells collide with one another and are separated. In addition, the stretching channel 202 is branched from the circular channel 201 and is designed to have a diameter 1.5 to 2.5 times the diameter of the cells. As such, the flux of the fluid discharged from the circular channel 201 to the stretching channel 202 increases, and ultimately cells are stretched and the binding force between the cells is weakened.

Subsequently, the cells that have passed through the stretching channel 202 are collected in the circular channel 201 of the next unit cell distribution channel 210. Here, due to the flux of the fluid flowing in the stretching channel 202, the cells collide with one another in the circular channel 201 and are distributed individually.

As the process of stretching and colliding in the unit cell distribution channel 210 is repeated, 80% of more of the clustered cells are separated as single cells. The effect of cell distribution through the cell distribution channel 120 can be identified in FIG. 5.

Figure 5:
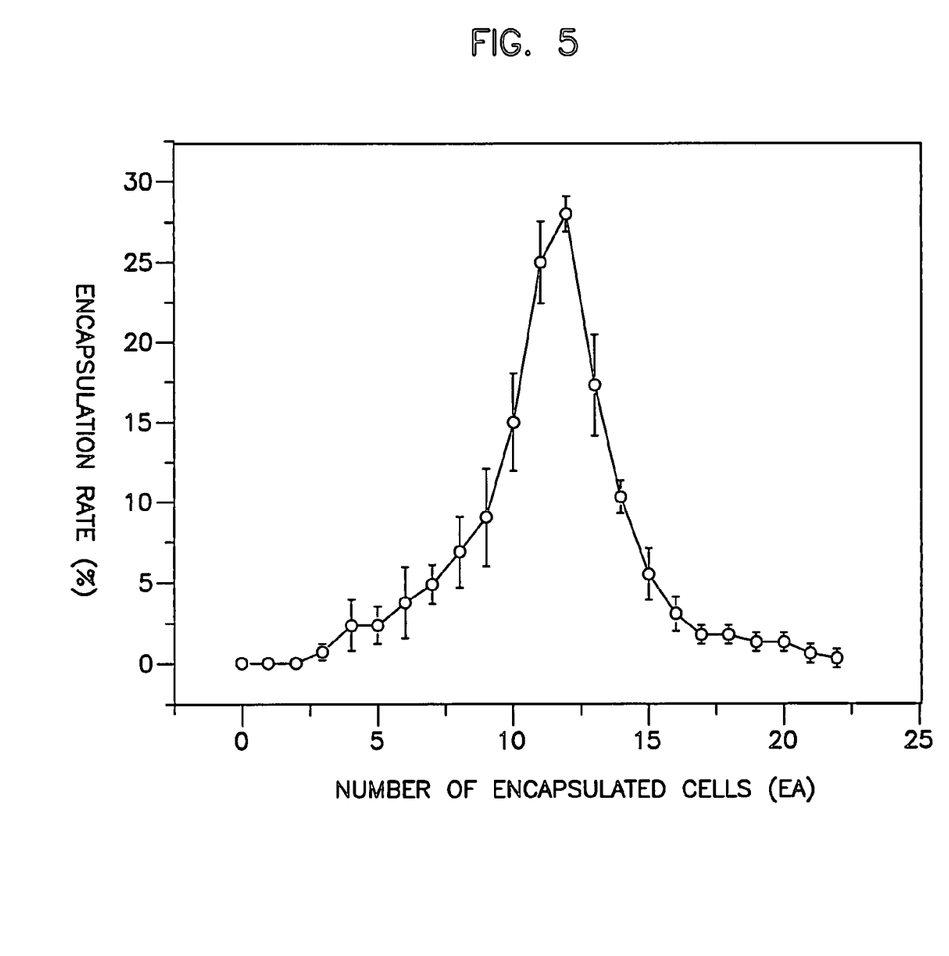
FIG. 5 is a graph showing the distribution of number of cells in the microcapsule formed by an apparatus for fabricating a microcapsule according to an embodiment of the present invention.

FIG. 5 is a graph showing the distribution of number of cells in the microcapsule formed by an apparatus for fabricating a microcapsule according to an embodiment of the present invention. As seen in FIG. 5, encapsulation rate is 85%, and 10 to 15 cells are uniformly distributed in a capsule. The standard deviation of the distribution shown in FIG. 5 is 0.5 to 3.16, indicating that the number of cells in the capsule is very constant.

The individually separated cells are supplied to the droplet forming unit A, where the dropletization inducing fluid supply channel 110 and the cells/cell dropletizing material supply channel 130 join, along with the cell dropletizing material.

Droplet Formation

As described above, the droplet forming unit A is the portion where the dropletization inducing fluid supply channel 110 and the cells/cell dropletizing material supply channel 130 join. In the droplet forming unit A, the individually separated cells supplied from the cells/cell dropletizing material supply channel 130, the cell dropletizing material, and the dropletization inducing fluid supplied from the dropletization inducing fluid supply channel 110 join with one another. That is, the cells, the cell dropletizing material and the dropletization inducing fluid join in the droplet forming unit A.

In one embodiment, the dropletization inducing fluid is oleic acid, which has a characteristic similar to that of oil, with high viscosity. As such, when the cells, the cell dropletizing material and the dropletization inducing fluid join in the droplet forming unit A, the cell dropletizing material surrounds the cells and turns into a spherical droplet due to surface tension.

Consequently, a droplet is formed in which the cells are surrounded by the cell dropletizing material. The cell dropletizing material may be alginic acid.

Through this process, the droplet comprising the cells and the cell dropletizing material is formed. The size of the droplet and the number of the cells inside the droplet can be controlled selectively. These can be controlled by controlling the flux of the cell dropletizing material supplied from the cell dropletizing material supply channel 140 and the flux of the cells/cell dropletizing material fluid mixture supplied from the cells/cell dropletizing material supply channel 130.

When the flux of the cell dropletizing material is relatively larger than the flux of the cells/cell dropletizing material fluid mixture, the number of the cells in the droplet decreases ant the size of the droplet increases. And, as the flux of the cell dropletizing material is relatively smaller than the flux of the cells/cell dropletizing material fluid mixture, the number of the cells in the droplet increases and the size of the droplet decreases.

Figure 6:
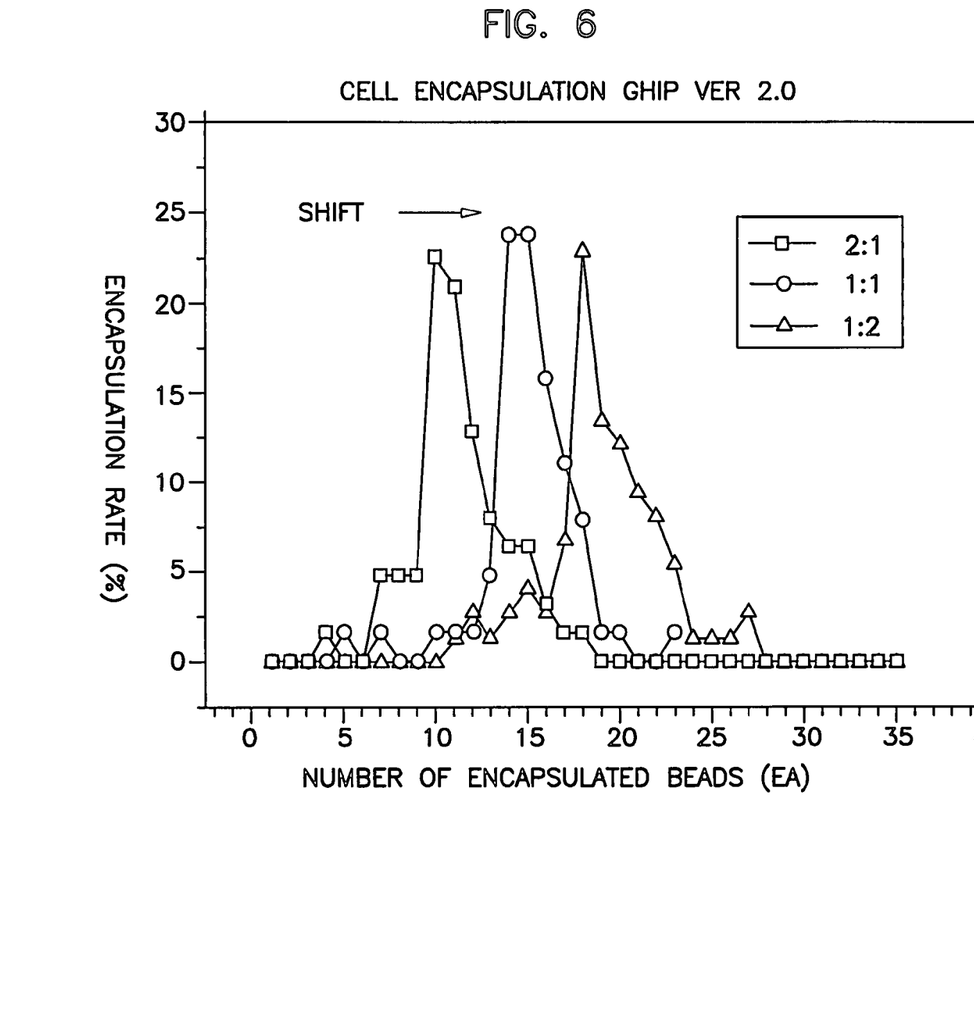
FIG. 6 is a graph showing the distribution of number of cells in the droplet when the flux of the cell dropletizing material an the flux of the cells/cell dropletizing material fluid mixture are set at 2:1, 1:1 and 1:2.

The change of the number of the cells inside the droplet depending on the flux of the cell dropletizing material and the flux of the cells/cell dropletizing material fluid mixture can be identified from FIG. 6. FIG. 6 is a graph showing the distribution of number of cells in the droplet when the flux of the cell dropletizing material an the flux of the cells/cell dropletizing material fluid mixture are set at 2:1, 1:1 and 1:2. As seen in FIG. 6, it is probable that the number of the cells inside the droplet is relatively smaller when the flux of the cell dropletizing material is high, and it is probable that the number of the cells inside the droplet is relatively larger when the flux of the cell dropletizing material is low.

Droplet Solidification

After the cells, the cell dropletizing material and the dropletization inducing fluid join in the droplet forming unit A and form the droplet by surface tension, the resultant droplets flow along the dropletization inducing fluid in the main channel 150. As the droplets flow along the length direction of the main channel 150, the cell dropletizing material comprised in the droplet reacts with calcium included in the dropletization inducing fluid.

As such, the droplet is formed into a bead, and ultimately into a microcapsule, which comprises the cells and the solidified cell dropletizing material. In other words, the droplet formed in the droplet forming unit A is turned into a microcapsule as it flows along the length direction of the main channel 150.

Fluid Exchange

The dropletization inducing fluid flowing in the main channel 150 includes calcium and promotes the solidification of the droplet, but it also reduces cell viability due to the toxicity of the dropletization inducing fluid itself. Therefore, once the solidification of the droplet is completed, that is once the microcapsule is formed, it is needed to exchange the dropletization inducing fluid in the main channel 150 with a neutral fluid having no effect on cell viability.

To this end, the neutral fluid supply channel 160 is provided downstream of the main channel 150. When the neutral fluid supplied from the neutral fluid supply channel 160 which is branched from one side of the main channel 150, the dropletization inducing fluid flowing in the main channel 150 is pushed to one side and is discharged through the dropletization inducing fluid discharge channel 170.

At this time, the stream line of the dropletization inducing fluid discharged through the dropletization inducing fluid discharge channel 170 is located outside the center of the microcapsule. As a result, the microcapsule keeps on flowing along the stream line of the neutral fluid, without being discharged through the dropletization inducing fluid discharge channel 170.

Figure 7:
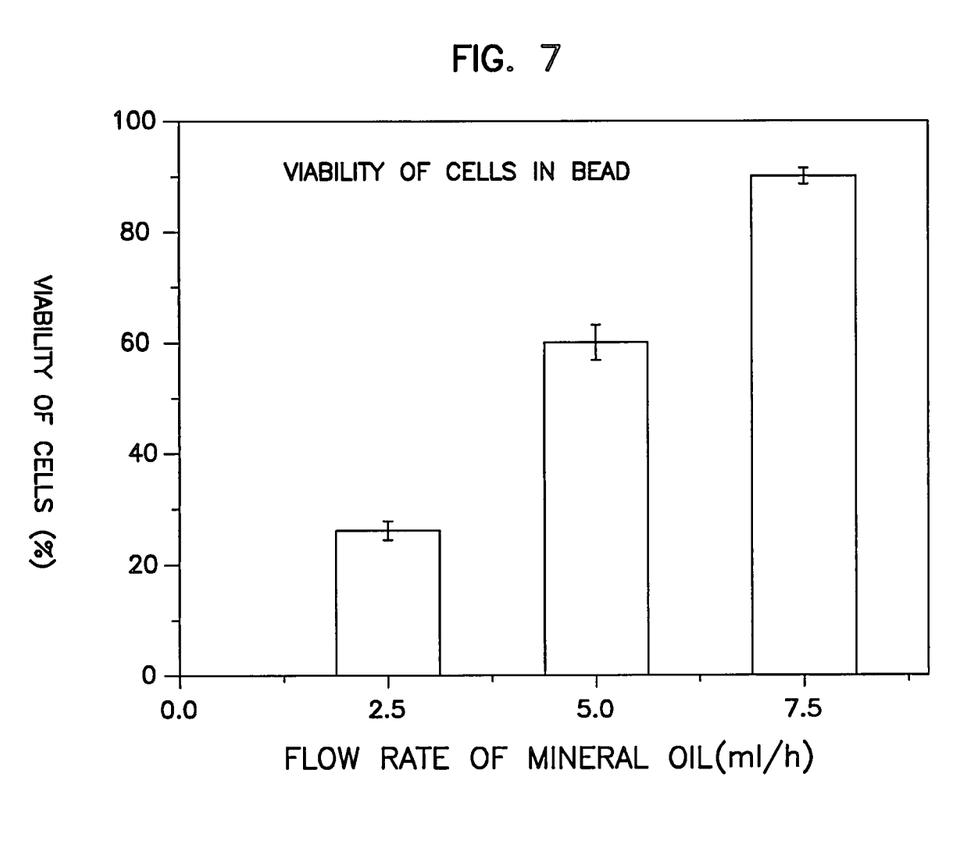
FIG. 7 is a graph showing the change of cell viability when the flux of the neutral fluid is set at 2.5 mL/h, 5.0 mL/h and 7.5 mL/h.

As the carrier fluid in the main channel 150 is changed from the dropletization inducing fluid to the neutral fluid, the viability of the cells inside the microcapsule is improved, which can be confirmed from FIG. 7. FIG. 7 is a graph showing the result of experiment in which the flux of the neutral fluid is set at 2.5 mL/h, 5.0 mL/h and 7.5 mL/h. When the flux of the neutral fluid was 2.5 mL/h, 30% or more of the dropletization inducing fluid flowing in the main channel 150 remained without being removed and was discharged through the capsule collection channel 180 as mixed with the neutral fluid and the microcapsule. As a result, the cell viability was as low as 26%.

When the flux of the neutral fluid was set at 5.0 mL/h, most of the dropletization inducing fluid flowing in the main channel 150 was discharged through the dropletization inducing fluid discharge channel 170, but approximately 5% of the dropletization inducing fluid was transferred through the capsule collection channel 180. As a result, a cell viability of 63% was observed.

At last, when the flux of the neutral fluid was set at 7.5 mL/h, all dropletization inducing fluid in the main channel 150 was discharged through the dropletization inducing fluid discharge channel 170, and a cell viability of 90% or better was observed. This result indicates that the cell viability can be improved through supply of the neutral fluid.

<Capsule Collection>

As the dropletization inducing fluid is discharged through the dropletization inducing fluid discharge channel 170, the fluid flowing in the main channel 150 is the neutral fluid and the microcapsule. The neutral fluid and the microcapsule are collected through the capsule collection channel 180 which is connected to one end of the main channel 150.

Occasionally, a small amount of the dropletization inducing fluid may be included in the fluid, in the process exchanging the dropletization inducing fluid with the neutral fluid. To cope with this situation, a dropletization inducing fluid auxiliary discharge channel 190 may further be provided.

The dropletization inducing fluid auxiliary discharge channel 190 may be designed to be branched from one end of the main channel 150, along with the capsule collection channel 180. Preferably, the diameter of the dropletization inducing fluid auxiliary discharge channel 190 is designed to be smaller than the diameter of the microcapsule in order to prevent the microcapsule from being discharged through the dropletization inducing fluid auxiliary discharge channel 190.

Figure 8:
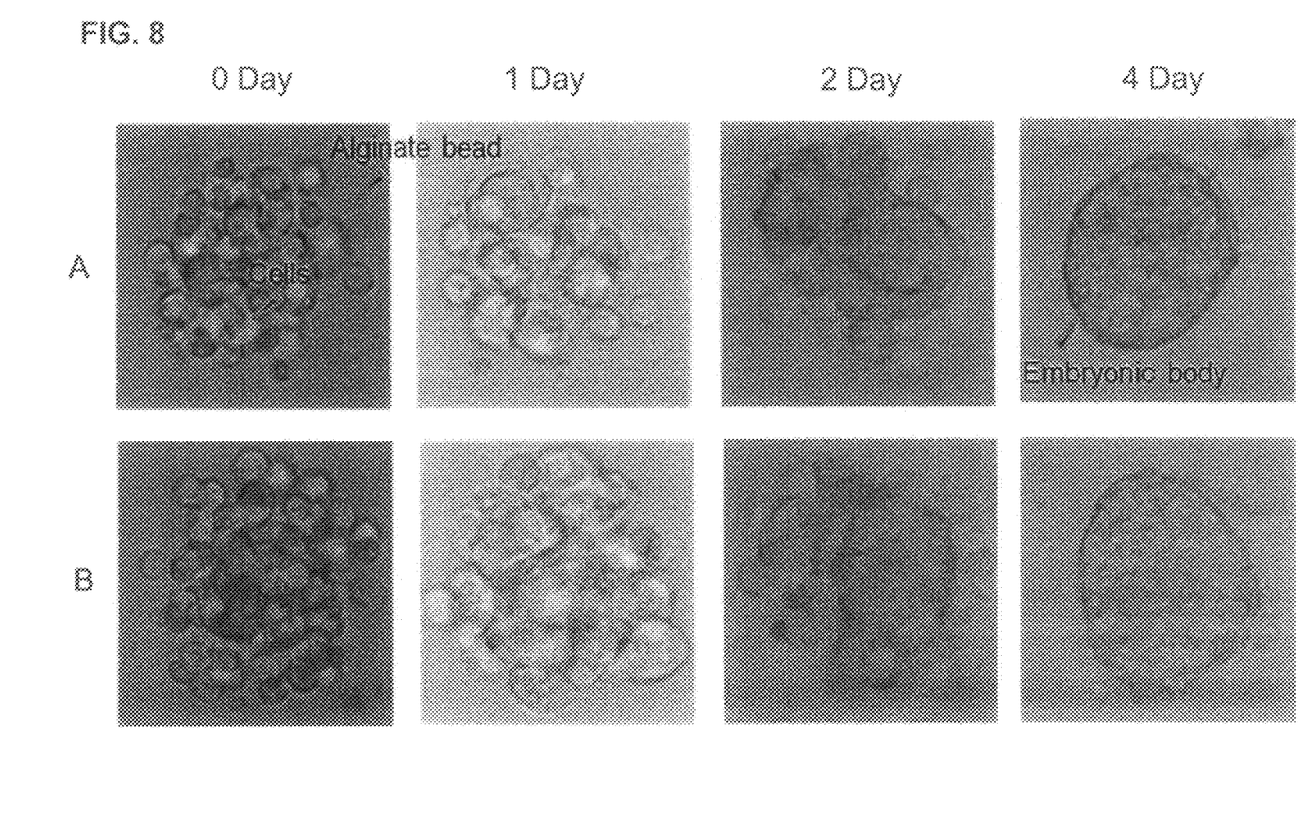
FIG. 8 shows photographs of an embryonic body formed using a microcapsule prepared according to an embodiment of the present invention.

Hereinabove, the action the apparatus for fabricating a microcapsule according to an embodiment of the present invention, that is the processes of 1) cell distribution, 2) droplet formation, 3) droplet solidification, 4) fluid exchange and 5) capsule collection, was explained. Cell culturing experiment was carried out for the microcapsule prepared using the apparatus for fabricating a microcapsule according to an embodiment of the present invention. As illustrated in FIG. 8, embryonic bodies with similar size were obtained with time. This indicates that the microcapsules prepared in accordance with the present invention exhibit uniform properties.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for fabricating a microcapsule using a plurality of microchannels which are spatially connected with one another and are designed such that fluid flows through them in a particular direction, comprising
    a cell supply unit comprising a cells and cell dropletizing material supply channel(130); and a cell dropletizing material supply channel(140) provided upstream of the cells and cell dropletizing material supply channel(130), wherein the cell supply unit supplies a fluid mixture of cells and a cell dropletizing material;
    a droplet forming unit, wherein a dropletization inducing fluid supply channel(110), the cells and cell dropletizing material supply channel(130) and a main channel(150) join with each other, and a dropletization inducing fluid supplied from the dropletization inducing fluid supply channel joins with the fluid mixture of the cells and the cell dropletizing material to form a droplet in the droplet forming unit and
    a fluid exchange unit comprising a neutral fluid supply channel (160), a dropletization inducing fluid discharge channel (170), and a portion of the main channel (150) between the neutral fluid supply channel (160) and the dropletization inducing fluid discharge channel (170), the neutral fluid supply channel being branched from the main channel, the dropletization inducing fluid discharge channel being branched from the main channel and provided downstream of the neutral fluid supply channel along the length direction of the main channel, wherein the main channel is a straight line channel, wherein the dropletization inducing fluid is exchanged with a neutral fluid not reacting with the cells in the fluid exchange unit.

2. The apparatus for fabricating a microcapsule as set forth in claim 1, further comprising a cell distribution unit comprising a plurality of connected unit cell distribution channels (210), wherein the cell distribution unit receives the fluid mixture of the cells and the cell dropletizing material form the cell supply unit and distributes the cells individually.

3. The apparatus for fabricating a microcapsule as set forth in claim 1, further comprising a capsule collection channel which is equipped at one end of the main channel and collects the microcapsule from the main channel.

4. The apparatus for fabricating a microcapsule as set forth in claim 1, wherein the cell dropletizing material is alginic acid.

5. The apparatus for fabricating a microcapsule as set forth in claim 1, wherein the dropletization inducing fluid is oleic acid.

6. The apparatus for fabricating a microcapsule as set forth in claim 1, wherein the neutral fluid is mineral oil or water.

7. An apparatus for fabricating a microcapsule using a plurality of microchannels which are spatially connected with one another and are designed such that fluid flows through them in a particular direction, comprising:
- a cell supply unit comprising a cells and cell dropletizing material supply channel(130); and a cell dropletizing material supply channel(140) provided upstream of the cells and cell dropletizing material supply channel(130), wherein the cell supply unit supplies a fluid mixture of cells and a cell dropletizing material;
- a droplet forming unit, wherein a dropletization inducing fluid supply channel(110), the cells and cell dropletizing material supply channel(130) and a main channel(150) join with each other, and a dropletization inducing fluid supplied from the dropletization inducing fluid supply channel joins with the fluid mixture of the cells and the cell dropletizing material to form a droplet in the droplet forming unit;
- a fluid exchange unit comprising a neutral fluid supply channel (160), a dropletization inducing fluid discharge channel (170), and a portion of the main channel (150) between the neutral fluid supply channel (160) and the dropletization inducing fluid discharge channel (170), the neutral fluid supply channel being branched from the main channel, the dropletization inducing fluid discharge channel being branched from the main channel and provided downstream of the neutral fluid supply channel along the length direction of the main channel, wherein the dropletization inducing fluid is exchanged with a neutral fluid not reacting with the cells in the fluid exchange unit; and
- a cell distribution unit comprising a plurality of connected unit cell distribution channels(210), the cell distribution unit receiving the fluid mixture of the cells and the cell dropletizing material form the cell supply unit and distributes the cells individually,
- wherein each unit cell distribution channel comprises an upstream circular channel, a down stream circular channel, and at least one stretching channel connecting the upstream circular channel to the downstream circular channel, wherein adjacent unit cell distribution channels are connected to each other such that a downstream circular channel on one unit cell distribution channel is connected to an upstream circular channel on the next adjacent downstream unit cell distribution channel.

8. The apparatus for fabricating a microcapsule as set forth in claim 7, wherein the stretching channel is branched from the circular channel, and the diameter of the stretching channel is smaller than the diameter of the circular channel.

9. The apparatus for fabricating a microcapsule as set forth in claim 8, wherein the diameter of the stretching channel is 1.5 to 2.5 times the diameter of the cells.

10. The apparatus for fabricating a microcapsule as set forth in claim 7, wherein a plurality of stretching channels are branched from one circular channel.

11. An apparatus for fabricating a microcapsule using a plurality of microchannels which are spatially connected with one another and are designed such that fluid flows through them in a particular direction, comprising:
- a cell supply unit comprising a cells and cell dropletizing material supply channel(130); and a cell dropletizing material supply channel(140) provided upstream of the cells and cell dropletizing material supply channel(130), wherein the cell supply unit supplies a fluid mixture of cells and a cell dropletizing material;
- a droplet forming unit, wherein a dropletization inducing fluid supply channel(110), the cells and cell dropletizing material supply channel(130) and a main channel(150) join with each other, and a dropletization inducing fluid supplied from the dropletization inducing fluid supply channel joins with the fluid mixture of the cells and the cell dropletizing material to form a droplet in the droplet forming unit;
- a fluid exchange unit comprising a neutral fluid supply channel (160), a dropletization inducing fluid discharge channel (170), and a portion of the main channel (150) between the neutral fluid supply channel (160) and the dropletization inducing fluid discharge channel (170), the neutral fluid supply channel being branched from the main channel, the dropletization inducing fluid discharge channel being branched from the main channel and provided downstream of the neutral fluid supply channel along the length direction of the main channel, wherein the dropletization inducing fluid is exchanged with a neutral fluid not reacting with the cells in the fluid exchange unit;
- a dropletization inducing fluid discharge channel which is branched from one side of the main channel and discharges the dropletization inducing fluid out of the main channel; and
- a dropletization inducing fluid auxiliary discharge channel which discharges the dropletization inducing fluid remaining without being discharged through the dropletization inducing fluid discharge channel, wherein the dropletization inducing fluid auxiliary discharge channel being connected to one end of the main channel.

12. The apparatus for fabricating a microcapsule as set forth in claim 11, wherein the diameter of the dropletization inducing fluid auxiliary discharge channel is smaller than the diameter of the capsule collection channel.

13. The apparatus for fabricating a microcapsule as set forth in claim 11, wherein the capsule collection channel and the dropletization inducing fluid auxiliary discharge channel are branched from one end of the main channel.

* * * * *